(12) United States Patent
Bryant (10) Patent No.: US 10,004,504 B2
(45) Date of Patent: *Jun. 26, 2018

(54) ADAPTER FOR POWERED SURGICAL DEVICES

(71) Applicant: Covidien LP, Mansfield, MA (US)

(72) Inventor: Teddy R. Bryant, San Francisco, CA (US)

(73) Assignee: Covidien LP, Mansfield, MA (US)

( * ) Notice: Subject to any disclaimer, the term of this patent is extended or adjusted under 35 U.S.C. 154(b) by 183 days.

This patent is subject to a terminal disclaimer.

(21) Appl. No.: 15/002,489

(22) Filed: Jan. 21, 2016

(65) Prior Publication Data

US 2016/0135810 A1 May 19, 2016

Related U.S. Application Data

(63) Continuation of application No. 13/621,859, filed on Sep. 18, 2012, now Pat. No. 9,282,963, which is a
(Continued)

(51) Int. Cl.
*A61B 17/072* (2006.01)
*A61B 17/10* (2006.01)
(Continued)

(52) U.S. Cl.
CPC .......... *A61B 17/105* (2013.01); *A61B 17/068* (2013.01); *A61B 17/0686* (2013.01);
(Continued)

(58) Field of Classification Search
CPC . A61B 17/068; A61B 17/0686; A61B 17/072; A61B 17/07207; A61B 17/105;
(Continued)

(56) References Cited

U.S. PATENT DOCUMENTS 319,071 A 6/1885 Colesworthy
529,401 A 11/1894 McCoy et al.
(Continued)

FOREIGN PATENT DOCUMENTS

AU 2008229795 A1 4/2009
CA 2451558 A1 1/2003
(Continued)

OTHER PUBLICATIONS

Extended European Search Report from EP Application No. 13172400.7 dated Jan. 21, 2014.
(Continued)

*Primary Examiner* — Scott A. Smith (57) ABSTRACT

An adapter assembly for selectively interconnecting a surgical end effector including at least one axially translatable drive member and a powered actuator device including at least one rotatable drive shaft is provided. The adapter assembly includes an actuation shaft configured to convert rotation of a first drive shaft of the powered actuator device into an axial translation of a first drive member of the surgical end effector. The adapter assembly further includes an elongate tube configured to convert rotation of a second drive shaft of the powered actuator device into an axial translation of a second drive member of the surgical end effector. The actuation shaft is disposed within the elongate tube, and the actuation shaft and the elongate tube translate axially independent of each other.

17 Claims, 5 Drawing Sheets

Related U.S. Application Data continuation of application No. 13/216,330, filed on Aug. 24, 2011, now Pat. No. 8,292,150.

(60) Provisional application No. 61/409,132, filed on Nov. 2, 2010.

(51) Int. Cl.
   *A61B 17/068* (2006.01)
   *A61B 17/00* (2006.01)
   *A61B 17/29* (2006.01)

(52) U.S. Cl.
   CPC ...... *A61B 17/072* (2013.01); *A61B 17/07207* (2013.01); *A61B 2017/00398* (2013.01); *A61B 2017/00477* (2013.01); *A61B 2017/00734* (2013.01); *A61B 2017/07214* (2013.01); *A61B 2017/2938* (2013.01); *A61B 2017/2943* (2013.01)

(58) Field of Classification Search
   CPC ........ A61B 17/115; A61B 2017/07214; A61B 2017/00398; A61B 2017/00477; A61B 2017/00734
   USPC .............. 227/19, 175.1, 175.2, 176.1, 180.1; 606/139, 151, 153, 219
   See application file for complete search history.

(56) References Cited

U.S. PATENT DOCUMENTS

| | | |
|---|---|---|
| 931,327 A | 8/1909 | Manzel |
| 935,977 A | 10/1909 | Haskell |
| 948,492 A | 2/1910 | Avery |
| 986,829 A | 3/1911 | Kasperson |
| 1,372,577 A | 3/1921 | Wallenberg |
| 1,414,207 A | 4/1922 | Reed |
| 1,414,460 A | 5/1922 | Dixon |
| 1,629,547 A | 5/1927 | Smith |
| 1,666,292 A | 4/1928 | Knudsen |
| 1,708,378 A | 4/1929 | Dale |
| 1,859,426 A | 5/1932 | Beremand |
| 1,961,036 A | 5/1934 | Boyle |
| 2,251,470 A | 8/1941 | Stacey |
| 2,284,982 A | 6/1942 | Miller |
| 2,289,583 A | 7/1942 | Malone |
| 2,361,683 A | 10/1944 | Greenberg |
| 2,398,924 A | 4/1946 | Daniels |
| 2,399,536 A | 4/1946 | Baum |
| 2,407,471 A | 9/1946 | Burk |
| 2,421,174 A | 5/1947 | Wyrick |
| 2,432,860 A | 12/1947 | Clatfelter |
| 2,449,284 A | 9/1948 | Dorman |
| 2,465,309 A | 3/1949 | Happe et al. |
| 2,478,195 A | 8/1949 | Hull |
| 2,482,995 A | 9/1949 | Willis |
| 2,483,662 A | 10/1949 | Niederhiser |
| 2,485,799 A | 10/1949 | Woytych |
| 2,511,416 A | 6/1950 | Rundorff |
| 2,529,396 A | 11/1950 | Hunt |
| 2,588,267 A | 3/1952 | McLaughlin |
| 2,598,477 A | 5/1952 | Wilberschied |
| 2,616,274 A | 11/1952 | Landrum |
| 2,676,025 A | 4/1954 | Davis |
| 2,680,634 A | 6/1954 | Haworth et al. |
| 2,695,787 A | 11/1954 | Sunnen |
| 2,709,600 A | 5/1955 | Lehde |
| 2,714,026 A | 7/1955 | Schultz |
| 2,719,722 A | 10/1955 | Nickless |
| 2,729,076 A | 1/1956 | Thomson |
| 2,730,220 A | 1/1956 | Dodd |
| 2,730,876 A | 1/1956 | Russell |
| 2,731,006 A | 1/1956 | Hensel |
| 2,777,340 A | 1/1957 | Hettwer et al. |
| 2,783,050 A | 2/1957 | Garrison et al. |
| 2,805,073 A | 9/1957 | Fletcher |
| 2,850,287 A | 9/1958 | Jackson |
| 2,851,295 A | 9/1958 | Chaffee |
| 2,857,166 A | 10/1958 | Conn et al. |
| 2,893,221 A | 7/1959 | Bell |
| 2,893,274 A | 7/1959 | Mueller et al. |
| 2,918,290 A | 12/1959 | Werstein |
| 2,918,291 A | 12/1959 | Plantas |
| 2,931,659 A | 4/1960 | Novkov |
| 2,940,765 A | 6/1960 | Appleby |
| 2,957,353 A | 10/1960 | Babacz |
| 2,998,258 A | 8/1961 | Ambrose |
| 3,023,015 A | 2/1962 | Pankow |
| 3,026,116 A | 3/1962 | Marini, Sr. |
| 3,064,502 A | 11/1962 | Pittwood |
| 3,111,328 A | 11/1963 | Di Rito et al. |
| 3,111,329 A | 11/1963 | Steinmann |
| 3,129,950 A | 4/1964 | Galler |
| 3,136,563 A | 6/1964 | Swanson et al. |
| 3,150,725 A | 9/1964 | Hornschuch et al. |
| 3,159,081 A | 12/1964 | Erikson |
| 3,202,433 A | 8/1965 | Davis |
| 3,210,962 A | 10/1965 | Birdwell |
| 3,211,485 A | 10/1965 | Petersen |
| 3,360,861 A | 1/1968 | Hoffman |
| 3,368,369 A | 2/1968 | Kimmel |
| 3,368,371 A | 2/1968 | Herman, Jr. |
| 3,383,883 A | 5/1968 | Dutaret |
| 3,506,277 A | 4/1970 | Harms |
| 3,516,311 A | 6/1970 | Marca |
| 3,521,507 A | 7/1970 | Yogus et al. |
| 3,540,748 A | 11/1970 | Buck |
| 3,553,980 A | 1/1971 | Dickinson et al. |
| 3,571,886 A | 3/1971 | Corsmeier |
| 3,610,643 A | 10/1971 | Thompson |
| 3,612,552 A | 10/1971 | Brundler |
| 3,657,941 A | 4/1972 | Engler |
| 3,658,352 A | 4/1972 | Koch et al. |
| 3,663,028 A | 5/1972 | King, Jr. et al. |
| 3,664,677 A | 5/1972 | Sunderman et al. |
| 3,680,435 A | 8/1972 | Deplante |
| 3,695,058 A | 10/1972 | Keith, Jr. |
| 3,696,984 A | 10/1972 | Fitchen |
| 3,707,301 A | 12/1972 | Rauls |
| 3,716,246 A | 2/1973 | Peterson |
| 3,724,237 A | 4/1973 | Wood |
| 3,730,540 A | 5/1973 | King, Jr. et al. |
| 3,734,515 A | 5/1973 | Dudek |
| 3,741,573 A | 6/1973 | Treer |
| 3,742,656 A | 7/1973 | Amos |
| 3,744,807 A | 7/1973 | Spires et al. |
| 3,746,353 A | 7/1973 | Allen |
| 3,747,946 A | 7/1973 | Edens |
| 3,750,498 A | 8/1973 | Willen |
| 3,750,671 A | 8/1973 | Hedrick |
| 3,752,595 A | 8/1973 | Woythal et al. |
| 3,756,737 A | 9/1973 | Smith |
| 3,758,125 A | 9/1973 | Cornelia |
| 3,759,336 A | 9/1973 | Marcovitz et al. |
| 3,779,063 A | 12/1973 | Gannon |
| 3,788,656 A | 1/1974 | Smith |
| 3,788,658 A | 1/1974 | Benjamin et al. |
| 3,815,380 A | 6/1974 | Esmay |
| 3,815,928 A | 6/1974 | Komori |
| 3,828,580 A | 8/1974 | Armbruster |
| 3,837,759 A | 9/1974 | Bittern |
| 3,843,143 A | 10/1974 | Laxson |
| 3,854,536 A | 12/1974 | Hallock, Jr. |
| 3,874,688 A | 4/1975 | Schiller |
| 3,884,120 A | 5/1975 | Diferdinando |
| 3,907,312 A | 9/1975 | Fletcher et al. |
| 3,913,952 A | 10/1975 | Matsui et al. |
| 3,945,221 A | 3/1976 | Miokovic |
| 3,955,377 A | 5/1976 | Bendall |
| 3,973,784 A | 8/1976 | Smith |
| 3,977,687 A | 8/1976 | Manganelli |
| 3,985,368 A | 10/1976 | Better et al. |
| 3,998,372 A | 12/1976 | Leonardo et al. |

(56) References Cited

U.S. PATENT DOCUMENTS

| | | |
|---|---|---|
| 4,006,996 A | 2/1977 | Kasabian |
| 4,007,795 A | 2/1977 | Gawron et al. |
| 4,017,934 A | 4/1977 | Callahan |
| 4,018,062 A | 4/1977 | Bulliot |
| 4,019,344 A | 4/1977 | Calistrat |
| 4,023,405 A | 5/1977 | Larson |
| 4,035,100 A | 7/1977 | Kruger et al. |
| D245,395 S | 8/1977 | Cognevich |
| 4,069,826 A | 1/1978 | Sessions et al. |
| 4,109,488 A | 8/1978 | Work |
| 4,158,522 A | 6/1979 | Wirfelt |
| 4,171,821 A | 10/1979 | Miller |
| 4,176,991 A | 12/1979 | Egli |
| 4,192,320 A | 3/1980 | Megahed |
| 4,197,886 A | 4/1980 | MacDonald |
| 4,224,969 A | 9/1980 | Plessner |
| 4,237,659 A | 12/1980 | Welsch et al. |
| 4,237,703 A | 12/1980 | Wahl, Jr. |
| 4,238,167 A | 12/1980 | Brugger et al. |
| 4,254,674 A | 3/1981 | Strussion et al. |
| 4,274,269 A | 6/1981 | Trabue |
| 4,274,774 A | 6/1981 | Haga et al. |
| D260,355 S | 8/1981 | Buzzell |
| 4,292,027 A | 9/1981 | Richmond |
| 4,298,208 A | 11/1981 | Benjamin et al. |
| 4,349,023 A | 9/1982 | Gross |
| 4,349,929 A | 9/1982 | Dewey |
| 4,362,166 A | 12/1982 | Furler et al. |
| 4,365,397 A | 12/1982 | Felpel |
| 4,384,669 A | 5/1983 | Welsh |
| 4,392,499 A | 7/1983 | Towse |
| 4,398,886 A | 8/1983 | Schuss et al. |
| 4,412,096 A | 10/1983 | Edgerton et al. |
| 4,434,927 A | 3/1984 | Butler et al. |
| 4,436,463 A | 3/1984 | Rea |
| 4,447,177 A | 5/1984 | Ochiai et al. |
| 4,449,953 A | 5/1984 | Nikomarov et al. |
| 4,452,592 A | 6/1984 | Tsai |
| 4,477,095 A | 10/1984 | Atkinson, III |
| 4,492,230 A | 1/1985 | Sunago et al. |
| 4,496,163 A | 1/1985 | Bernfeld |
| 4,500,235 A | 2/1985 | Johnsen |
| 4,504,227 A | 3/1985 | Lohn |
| 4,559,043 A | 12/1985 | Whitehouse et al. |
| 4,560,310 A | 12/1985 | Eckstein et al. |
| 4,570,633 A | 2/1986 | Golden |
| 4,575,015 A | 3/1986 | Sugioka et al. |
| 4,575,359 A | 3/1986 | Bermingham |
| 4,597,699 A | 7/1986 | Ramunas |
| 4,614,137 A | 9/1986 | Jones |
| 4,616,651 A | 10/1986 | Golden |
| 4,645,453 A | 2/1987 | Niznick |
| 4,647,051 A | 3/1987 | Stone et al. |
| 4,655,631 A | 4/1987 | Mitchell |
| 4,661,009 A | 4/1987 | Tripp |
| 4,668,138 A | 5/1987 | Carter |
| 4,674,172 A | 6/1987 | Botimer |
| 4,685,687 A | 8/1987 | Hall et al. |
| 4,688,810 A | 8/1987 | Waite |
| 4,691,429 A | 9/1987 | Goodsmith |
| 4,708,548 A | 11/1987 | Taylor et al. |
| 4,710,079 A | 12/1987 | Smith et al. |
| 4,722,645 A | 2/1988 | Regan |
| 4,722,685 A | 2/1988 | de Estrada et al. |
| 4,750,750 A | 6/1988 | Batalorf, Jr. |
| 4,772,245 A | 9/1988 | Readman et al. |
| 4,777,714 A | 10/1988 | Blessing |
| 4,781,654 A | 11/1988 | Walter et al. |
| 4,786,221 A | 11/1988 | March |
| 4,793,053 A | 12/1988 | Zuccaro et al. |
| 4,795,291 A | 1/1989 | March |
| 4,809,995 A | 3/1989 | Ramunas |
| 4,810,139 A | 3/1989 | Regan |
| 4,815,347 A | 3/1989 | Rogers |
| 4,818,157 A | 4/1989 | Kouvelis |
| 4,823,807 A | 4/1989 | Russell et al. |
| 4,824,298 A | 4/1989 | Lippacher et al. |
| 4,834,596 A | 5/1989 | Hollifield et al. |
| 4,836,826 A | 6/1989 | Carter |
| 4,838,361 A | 6/1989 | O'Toole |
| 4,840,520 A | 6/1989 | Pfalzgraf |
| 4,861,203 A | 8/1989 | Bassett et al. |
| 4,861,313 A | 8/1989 | Zeiser et al. |
| 4,870,743 A | 10/1989 | Gilmore |
| 4,874,181 A | 10/1989 | Hsu |
| 4,879,930 A | 11/1989 | Von Haas |
| 4,886,402 A | 12/1989 | Pfalzgraf |
| 4,910,860 A | 3/1990 | Winkler et al. |
| 4,913,607 A | 4/1990 | von Haas |
| 4,919,023 A | 4/1990 | Bloink |
| 4,938,731 A | 7/1990 | Nguyen et al. |
| 4,941,861 A | 7/1990 | Painter |
| 4,946,177 A | 8/1990 | Barbieux |
| 4,958,966 A | 9/1990 | Andrews |
| 4,958,968 A | 9/1990 | von Haas et al. |
| 4,969,863 A | 11/1990 | van't Hooft et al. |
| 4,995,768 A | 2/1991 | Craft |
| 4,998,934 A | 3/1991 | Bernstein |
| 5,011,344 A | 4/1991 | Johnson |
| 5,015,129 A | 5/1991 | Albin |
| 5,033,921 A | 7/1991 | Yasuhara et al. |
| 5,049,071 A | 9/1991 | Davis et al. |
| 5,052,496 A | 10/1991 | Albert et al. |
| 5,062,749 A | 11/1991 | Sheets |
| 5,084,692 A | 1/1992 | Finch et al. |
| 5,098,416 A | 3/1992 | Imonti |
| 5,110,145 A | 5/1992 | Stewart |
| 5,129,118 A | 7/1992 | Walmesley |
| 5,135,060 A | 8/1992 | Ide |
| 5,137,495 A | 8/1992 | Luebke |
| 5,173,017 A | 12/1992 | Oshnock et al. |
| 5,180,261 A | 1/1993 | Schreiber |
| 5,190,422 A | 3/1993 | Lechot |
| 5,190,529 A | 3/1993 | McCrory et al. |
| 5,191,666 A | 3/1993 | Corbin |
| 5,192,206 A | 3/1993 | Davis et al. |
| 5,193,826 A | 3/1993 | Smith |
| 5,203,595 A | 4/1993 | Borzone et al. |
| 5,209,219 A | 5/1993 | Hollobaugh |
| 5,219,174 A | 6/1993 | Zurbrugg et al. |
| 5,224,898 A | 7/1993 | Johnson et al. |
| 5,236,356 A | 8/1993 | Davis et al. |
| 5,238,341 A | 8/1993 | Horsch |
| 5,282,638 A | 2/1994 | Harper |
| 5,301,061 A | 4/1994 | Nakada et al. |
| 5,306,146 A | 4/1994 | Davis et al. |
| 5,318,529 A | 6/1994 | Kontos |
| 5,330,206 A | 7/1994 | Krumszyn et al. |
| 5,342,195 A | 8/1994 | Davis et al. |
| 5,352,074 A | 10/1994 | Ishikawa |
| 5,368,421 A | 11/1994 | Head |
| 5,392,662 A | 2/1995 | Jadrich et al. |
| 5,411,508 A | 5/1995 | Bessler et al. |
| 5,427,087 A | 6/1995 | Ito et al. |
| 5,431,661 A | 7/1995 | Koch |
| 5,439,005 A | 8/1995 | Vaughn |
| 5,447,472 A | 9/1995 | Ide |
| 5,476,379 A | 12/1995 | Disel |
| 5,489,205 A | 2/1996 | Davis et al. |
| 5,501,542 A | 3/1996 | Hall, Sr. |
| 5,507,787 A | 4/1996 | Borghi |
| 5,509,489 A | 4/1996 | Lower, Jr. |
| 5,514,113 A | 5/1996 | Anderson et al. |
| 5,540,375 A | 7/1996 | Bolanos et al. |
| 5,540,706 A | 7/1996 | Aust et al. |
| 5,549,637 A | 8/1996 | Crainich |
| 5,549,657 A | 8/1996 | Stern et al. |
| 5,553,675 A | 9/1996 | Pitzen et al. |
| 5,564,615 A | 10/1996 | Bishop et al. |
| 5,564,717 A | 10/1996 | Alberts |
| 5,570,445 A | 10/1996 | Chou et al. |
| 5,586,847 A | 12/1996 | Mattern, Jr. et al. |
| 5,609,560 A | 3/1997 | Ichikawa et al. |
| 5,615,590 A | 4/1997 | Speckhahn |

(56) References Cited

U.S. PATENT DOCUMENTS

| | | |
|---|---|---|
| 5,632,432 A | 5/1997 | Schulze et al. |
| 5,653,694 A | 8/1997 | Powles et al. |
| 5,658,192 A | 8/1997 | Reinauer |
| 5,658,300 A | 8/1997 | Bito et al. |
| 5,667,228 A | 9/1997 | Fabris |
| 5,676,028 A | 10/1997 | Jordan |
| 5,678,961 A | 10/1997 | Fleege et al. |
| 5,693,025 A | 12/1997 | Stevens |
| 5,693,042 A | 12/1997 | Boiarski et al. |
| 5,701,910 A | 12/1997 | Powles et al. |
| 5,704,838 A | 1/1998 | Teale |
| 5,709,605 A | 1/1998 | Riefe et al. |
| 5,711,709 A | 1/1998 | McCoy |
| 5,716,056 A | 2/1998 | Bokram |
| 5,730,657 A | 3/1998 | Olgren |
| 5,741,134 A | 4/1998 | Davis |
| 5,743,431 A | 4/1998 | Brattesani |
| 5,746,724 A | 5/1998 | Powles et al. |
| 5,762,603 A | 6/1998 | Thompson |
| 5,775,857 A | 7/1998 | Johne |
| 5,782,396 A | 7/1998 | Mastri et al. |
| 5,785,229 A | 7/1998 | Franzini |
| 5,800,391 A | 9/1998 | Kontos |
| 5,806,859 A | 9/1998 | Saccomanno, III |
| 5,836,727 A | 11/1998 | Scheer |
| 5,863,159 A | 1/1999 | Lasko |
| 5,865,361 A | 2/1999 | Milliman et al. |
| 5,876,381 A | 3/1999 | Pond et al. |
| 5,893,689 A | 4/1999 | Juhasz |
| 5,901,967 A | 5/1999 | Morisaki |
| 5,902,280 A | 5/1999 | Powles et al. |
| 5,913,845 A | 6/1999 | Brimhall |
| 5,921,563 A | 7/1999 | Huggins et al. |
| 5,928,241 A | 7/1999 | Menut et al. |
| 5,931,737 A | 8/1999 | Aota et al. |
| 5,944,331 A | 8/1999 | Kim |
| 5,957,634 A | 9/1999 | Carpinelli |
| 5,957,636 A | 9/1999 | Boisvert |
| 5,984,595 A | 11/1999 | Mizoguchi |
| 5,984,596 A | 11/1999 | Fehrle et al. |
| 5,993,454 A | 11/1999 | Longo |
| 6,003,416 A | 12/1999 | Ando et al. |
| 6,010,054 A | 1/2000 | Johnson et al. |
| 6,032,849 A | 3/2000 | Mastri et al. |
| 6,033,162 A | 3/2000 | Uebele et al. |
| 6,035,512 A | 3/2000 | Cook |
| 6,042,310 A | 3/2000 | Campbell et al. |
| 6,062,574 A | 5/2000 | Yorde |
| 6,062,779 A | 5/2000 | Sugimura |
| 6,074,304 A | 6/2000 | Olbrich et al. |
| 6,086,292 A | 7/2000 | Yokoyama |
| 6,098,726 A | 8/2000 | Taylor et al. |
| 6,109,620 A | 8/2000 | Roberts et al. |
| 6,126,549 A | 10/2000 | Appell et al. |
| 6,126,651 A | 10/2000 | Mayer |
| 6,129,547 A | 10/2000 | Cise et al. |
| 6,142,878 A | 11/2000 | Barin |
| 6,145,851 A | 11/2000 | Heber |
| 6,152,826 A | 11/2000 | Profeta et al. |
| 6,155,576 A | 12/2000 | Yorde |
| 6,159,102 A | 12/2000 | Hennessey et al. |
| 6,161,937 A | 12/2000 | Rosenstatter |
| 6,165,169 A | 12/2000 | Panescu et al. |
| 6,171,033 B1 | 1/2001 | Wrobel |
| 6,179,300 B1 | 1/2001 | Baumann et al. |
| 6,179,303 B1 | 1/2001 | Jansen |
| 6,186,712 B1 | 2/2001 | Senzaki |
| 6,190,395 B1 | 2/2001 | Williams |
| 6,193,241 B1 | 2/2001 | Robison |
| 6,193,242 B1 | 2/2001 | Robison |
| 6,200,220 B1 | 3/2001 | Drew |
| 6,203,435 B1 | 3/2001 | Falgout, Sr. |
| 6,213,071 B1 | 4/2001 | Lancefield et al. |
| 6,217,453 B1 | 4/2001 | Thompson |
| 6,224,304 B1 | 5/2001 | Smith et al. |
| 6,231,450 B1 | 5/2001 | Korus |
| 6,239,732 B1 | 5/2001 | Cusey |
| 6,241,139 B1 | 6/2001 | Milliman et al. |
| 6,241,434 B1 | 6/2001 | Ajimi |
| 6,250,856 B1 | 6/2001 | Miyanaga |
| 6,253,720 B1 | 7/2001 | Lancefield et al. |
| 6,260,281 B1 | 7/2001 | Okumura et al. |
| 6,264,086 B1 | 7/2001 | McGuckin, Jr. |
| 6,264,408 B1 | 7/2001 | Lung et al. |
| 6,276,065 B1 | 8/2001 | Osada et al. |
| 6,287,059 B1 | 9/2001 | Hashidate et al. |
| 6,287,117 B1 | 9/2001 | Niznick |
| 6,287,203 B1 | 9/2001 | Chen et al. |
| 6,287,207 B1 | 9/2001 | Rui et al. |
| 6,293,559 B1 | 9/2001 | Harman, Jr. et al. |
| 6,296,096 B1 | 10/2001 | Chludek |
| 6,299,538 B1 | 10/2001 | Gassmann |
| 6,302,311 B1 | 10/2001 | Adams et al. |
| 6,302,409 B1 | 10/2001 | Gutsche |
| 6,305,519 B1 | 10/2001 | Katoh et al. |
| 6,308,669 B1 | 10/2001 | Lancefield et al. |
| 6,312,255 B1 | 11/2001 | Hudak |
| 6,312,339 B1 | 11/2001 | Beyert |
| 6,315,060 B1 | 11/2001 | Schuda et al. |
| 6,321,855 B1 | 11/2001 | Barnes |
| 6,343,731 B1 | 2/2002 | Adams et al. |
| 6,357,974 B1 | 3/2002 | Robins |
| 6,368,324 B1 | 4/2002 | Dinger et al. |
| 6,371,705 B1 | 4/2002 | Gaudreau |
| 6,371,909 B1 | 4/2002 | Hoeg et al. |
| 6,375,577 B1 | 4/2002 | Smith et al. |
| 6,378,630 B1 | 4/2002 | Ritorto et al. |
| 6,464,589 B1 | 10/2002 | Shinozuka |
| 6,478,681 B1 | 11/2002 | Overaker et al. |
| 6,484,859 B2 | 11/2002 | Chludek |
| 6,506,120 B1 | 1/2003 | Lockwood |
| 6,510,970 B2 | 1/2003 | McLean et al. |
| 6,511,268 B1 | 1/2003 | Vasudeva et al. |
| 6,511,321 B1 | 1/2003 | Trushkowsky et al. |
| 6,517,560 B1 | 2/2003 | Toth et al. |
| 6,533,157 B1 | 3/2003 | Whitman |
| 6,533,578 B2 | 3/2003 | Segal |
| 6,537,280 B2 | 3/2003 | Dinger et al. |
| 6,554,288 B2 | 4/2003 | Tomoni |
| 6,554,290 B2 | 4/2003 | Lin |
| 6,569,118 B2 | 5/2003 | Johnson et al. |
| 6,569,163 B2 | 5/2003 | Hata et al. |
| 6,585,462 B1 | 7/2003 | Goransson |
| 6,604,744 B2 | 8/2003 | Monge |
| 6,610,066 B2 | 8/2003 | Dinger et al. |
| 6,612,586 B2 | 9/2003 | Liou |
| 6,615,835 B1 | 9/2003 | Cise et al. |
| 6,616,446 B1 | 9/2003 | Schmid |
| 6,619,413 B2 | 9/2003 | Hamilton et al. |
| 6,640,150 B1 | 10/2003 | Persson et al. |
| 6,640,679 B1 | 11/2003 | Roberts, Jr. |
| 6,640,911 B2 | 11/2003 | Lieser et al. |
| 6,645,218 B1 | 11/2003 | Cassidy et al. |
| 6,654,999 B2 | 12/2003 | Stoddard et al. |
| 6,663,493 B1 | 12/2003 | Chen |
| 6,666,114 B1 | 12/2003 | Lin |
| 6,669,568 B1 | 12/2003 | Neuner et al. |
| 6,679,365 B2 | 1/2004 | Katoh et al. |
| 6,702,680 B2 | 3/2004 | Sullivan et al. |
| 6,716,028 B2 | 4/2004 | Rahman et al. |
| 6,722,038 B2 | 4/2004 | Visman et al. |
| 6,725,004 B2 | 4/2004 | Ahn et al. |
| 6,743,240 B2 | 6/2004 | Smith et al. |
| 6,755,424 B1 | 6/2004 | Paulsen |
| 6,761,361 B2 | 7/2004 | Taylor et al. |
| 6,769,846 B2 | 8/2004 | Campbell, Jr. et al. |
| 6,783,533 B2 | 8/2004 | Green et al. |
| 6,793,652 B1 | 9/2004 | Whitman et al. |
| 6,808,345 B2 | 10/2004 | Kato |
| 6,817,508 B1 | 11/2004 | Racenet et al. |
| 6,824,566 B2 | 11/2004 | Kana et al. |
| 6,825,630 B2 | 11/2004 | Katoh et al. |
| 6,830,174 B2 | 12/2004 | Hillstead et al. |
| 6,849,071 B2 | 2/2005 | Whitman et al. |

(56) References Cited

U.S. PATENT DOCUMENTS

| | | |
|---|---|---|
| 6,854,740 B2 | 2/2005 | Baumann et al. |
| 6,854,741 B2 | 2/2005 | Lopez |
| 6,893,026 B2 | 5/2005 | Yoshimura et al. |
| 6,899,538 B2 | 5/2005 | Matoba |
| 6,905,057 B2 | 6/2005 | Swayze et al. |
| 6,915,865 B2 | 7/2005 | Boyd |
| 6,916,248 B1 | 7/2005 | Burgess |
| 6,926,526 B2 | 8/2005 | Hudak |
| 6,935,636 B2 | 8/2005 | Bobst |
| 6,935,637 B2 | 8/2005 | Cantlon |
| 6,955,660 B2 | 10/2005 | Fisher |
| 6,986,451 B1 | 1/2006 | Mastri et al. |
| 6,988,649 B2 | 1/2006 | Shelton, IV et al. |
| 7,011,661 B2 | 3/2006 | Riedel et al. |
| 7,014,464 B2 | 3/2006 | Niznick |
| 7,018,298 B1 | 3/2006 | Chiou |
| 7,032,798 B2 | 4/2006 | Whitman et al. |
| RE39,152 E | 6/2006 | Aust et al. |
| 7,059,508 B2 | 6/2006 | Shelton, IV et al. |
| 7,121,951 B2 | 10/2006 | Chang |
| 7,122,029 B2 | 10/2006 | Koop et al. |
| 7,137,185 B2 | 11/2006 | Voss et al. |
| 7,140,528 B2 | 11/2006 | Shelton, IV |
| 7,144,326 B2 | 12/2006 | Thompson |
| 7,147,138 B2 | 12/2006 | Shelton, IV |
| 7,150,680 B2 | 12/2006 | White |
| 7,153,214 B2 | 12/2006 | Delaney et al. |
| 7,172,104 B2 | 2/2007 | Scirica et al. |
| 7,182,558 B2 | 2/2007 | Haimer |
| 7,192,355 B2 | 3/2007 | Bayer et al. |
| 7,195,247 B2 | 3/2007 | Shu |
| 7,204,804 B2 | 4/2007 | Zirps et al. |
| 7,217,072 B1 | 5/2007 | Haimer |
| 7,225,964 B2 | 6/2007 | Mastri et al. |
| 7,228,767 B2 | 6/2007 | Chang |
| 7,238,021 B1 | 7/2007 | Johnson |
| 7,243,572 B1 | 7/2007 | Arling et al. |
| 7,267,548 B2 | 9/2007 | Ponzini |
| 7,270,568 B2 | 9/2007 | Osypka |
| 7,272,345 B2 | 9/2007 | Kim et al. |
| 7,284,936 B1 | 10/2007 | Rinner |
| 7,300,042 B2 | 11/2007 | McClure |
| 7,316,529 B2 | 1/2008 | Phillips et al. |
| 7,331,585 B2 | 2/2008 | Lindstrom |
| 7,331,738 B2 | 2/2008 | Hofbrucker et al. |
| 7,334,970 B2 | 2/2008 | Kozak |
| 7,338,420 B2 | 3/2008 | Imahata |
| 7,347,828 B2 | 3/2008 | Francese et al. |
| 7,354,230 B2 | 4/2008 | Bauman |
| 7,371,034 B2 | 5/2008 | Clark |
| 7,374,377 B2 | 5/2008 | Bauman |
| 7,407,078 B2 | 8/2008 | Shelton, IV et al. |
| 7,431,587 B2 | 10/2008 | Pond |
| 7,464,849 B2 | 12/2008 | Shelton, IV et al. |
| 7,481,824 B2 | 1/2009 | Boudreaux et al. |
| 7,488,134 B2 | 2/2009 | Kinme et al. |
| 7,491,058 B2 | 2/2009 | Jorneus et al. |
| 7,494,304 B2 | 2/2009 | McAuliffe |
| 7,506,877 B1 | 3/2009 | Henderson et al. |
| 7,534,104 B2 | 5/2009 | Schneider |
| 7,549,564 B2 | 6/2009 | Boudreaux |
| 7,549,953 B2 | 6/2009 | Walters |
| 7,565,993 B2 | 7/2009 | Milliman et al. |
| 7,575,144 B2 | 8/2009 | Ortiz et al. |
| 7,588,175 B2 | 9/2009 | Timm et al. |
| 7,607,207 B2 | 10/2009 | Buttau et al. |
| 7,648,315 B2 | 1/2010 | Omi et al. |
| 7,658,740 B2 | 2/2010 | Shores et al. |
| 7,690,999 B2 | 4/2010 | Nozaki et al. |
| 7,699,835 B2 | 4/2010 | Lee et al. |
| 7,708,182 B2 | 5/2010 | Viola |
| 7,721,931 B2 | 5/2010 | Shelton, IV et al. |
| 7,738,971 B2 | 6/2010 | Swayze et al. |
| 7,743,960 B2 | 6/2010 | Whitman et al. |
| 7,770,775 B2 | 8/2010 | Shelton, IV et al. |
| 7,793,812 B2 | 9/2010 | Moore et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,857,185 B2 | 12/2010 | Swayze et al. |
| 7,870,989 B2 | 1/2011 | Viola et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,182,494 B1 | 5/2012 | Yencho et al. |
| 8,186,587 B2 | 5/2012 | Zmood et al. |
| 8,235,273 B2 | 8/2012 | Olson et al. |
| 8,272,554 B2 | 9/2012 | Whitman et al. |
| 8,292,150 B2 | 10/2012 | Bryant |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,365,633 B2 | 2/2013 | Simaan et al. |
| 8,371,492 B2 | 2/2013 | Aranyi et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0005068 A1 | 6/2001 | Gifford et al. |
| 2001/0037114 A1 | 11/2001 | Dinger et al. |
| 2001/0039427 A1 | 11/2001 | Dinger et al. |
| 2001/0041321 A1 | 11/2001 | Segal |
| 2001/0042964 A1 | 11/2001 | Bedi et al. |
| 2001/0050465 A1 | 12/2001 | Gifford et al. |
| 2002/0003992 A1 | 1/2002 | Omi |
| 2002/0006830 A1 | 1/2002 | Buhren |
| 2002/0010433 A1 | 1/2002 | Johnson et al. |

(56) References Cited

U.S. PATENT DOCUMENTS

| | | |
|---|---|---|
| 2002/0032436 A1 | 3/2002 | Mogg |
| 2002/0049454 A1 | 4/2002 | Whitman et al. |
| 2002/0058958 A1 | 5/2002 | Walen |
| 2002/0093151 A1 | 7/2002 | Monge |
| 2002/0109308 A1 | 8/2002 | Ochoa |
| 2002/0128610 A1 | 9/2002 | Owades |
| 2002/0151902 A1 | 10/2002 | Riedel et al. |
| 2002/0165435 A1 | 11/2002 | Weiss |
| 2002/0165541 A1 | 11/2002 | Whitman |
| 2002/0165549 A1 | 11/2002 | Owusu-Akyaw et al. |
| 2003/0038938 A1 | 2/2003 | Jung et al. |
| 2003/0040784 A1 | 2/2003 | Pasternak et al. |
| 2003/0047891 A1 | 3/2003 | Tomoni |
| 2003/0073502 A1 | 4/2003 | Barnley et al. |
| 2003/0077935 A1 | 4/2003 | Stein et al. |
| 2003/0077943 A1 | 4/2003 | Osypka |
| 2003/0130677 A1 | 7/2003 | Whitman et al. |
| 2003/0165794 A1 | 9/2003 | Matoba |
| 2003/0171815 A1 | 9/2003 | Kana et al. |
| 2003/0190581 A1 | 10/2003 | Segal |
| 2004/0038175 A1 | 2/2004 | Hickok |
| 2004/0049162 A1 | 3/2004 | Fisher |
| 2004/0052598 A1 | 3/2004 | Haimer |
| 2004/0057806 A1 | 3/2004 | Campbell et al. |
| 2004/0075225 A1 | 4/2004 | Heim |
| 2004/0092991 A1 | 5/2004 | Deng |
| 2004/0133189 A1 | 7/2004 | Sakurai |
| 2004/0162149 A1 | 8/2004 | Bayer et al. |
| 2004/0166464 A1 | 8/2004 | Schneider |
| 2004/0167478 A1 | 8/2004 | Mooney et al. |
| 2004/0176739 A1 | 9/2004 | Stephens et al. |
| 2004/0176751 A1 | 9/2004 | Weitzner et al. |
| 2004/0215058 A1 | 10/2004 | Zirps et al. |
| 2004/0230267 A1 | 11/2004 | Wenger |
| 2004/0260355 A1 | 12/2004 | Holleman et al. |
| 2004/0260373 A1 | 12/2004 | Ries et al. |
| 2004/0262856 A1 | 12/2004 | Cantlon |
| 2004/0262857 A1 | 12/2004 | Lopez |
| 2005/0017049 A1 | 1/2005 | Betz |
| 2005/0021047 A1 | 1/2005 | Voss et al. |
| 2005/0025590 A1 | 2/2005 | Spadaccini |
| 2005/0131357 A1 | 6/2005 | Denton et al. |
| 2005/0131442 A1 | 6/2005 | Yachia et al. |
| 2005/0272280 A1 | 12/2005 | Osypka |
| 2005/0282102 A1 | 12/2005 | Kert |
| 2006/0015130 A1 | 1/2006 | Voorhees et al. |
| 2006/0020211 A1 | 1/2006 | Tokumoto et al. |
| 2006/0024639 A1 | 2/2006 | Pond |
| 2006/0025792 A1 | 2/2006 | Gibson et al. |
| 2006/0025793 A1 | 2/2006 | Gibson et al. |
| 2006/0041268 A1 | 2/2006 | Shores et al. |
| 2006/0068361 A1 | 3/2006 | Bergler et al. |
| 2006/0105844 A1 | 5/2006 | Sweet et al. |
| 2006/0110706 A1 | 5/2006 | Jorneus et al. |
| 2006/0142740 A1 | 6/2006 | Sherman et al. |
| 2006/0175773 A1 | 8/2006 | Tsai et al. |
| 2006/0223640 A1 | 10/2006 | Bassett et al. |
| 2006/0225540 A1 | 10/2006 | Tsai et al. |
| 2006/0278680 A1 | 12/2006 | Viola et al. |
| 2006/0287116 A1 | 12/2006 | White |
| 2007/0023476 A1 | 2/2007 | Whitman et al. |
| 2007/0023477 A1 | 2/2007 | Whitman et al. |
| 2007/0054232 A1 | 3/2007 | Rauchenzauner |
| 2007/0055219 A1 | 3/2007 | Whitman et al. |
| 2007/0106301 A1 | 5/2007 | Charles et al. |
| 2007/0108706 A1 | 5/2007 | Cornwell et al. |
| 2007/0145694 A1 | 6/2007 | Ullrich et al. |
| 2007/0152014 A1 | 7/2007 | Gillum et al. |
| 2007/0152408 A1 | 7/2007 | Peters |
| 2007/0175961 A1 | 8/2007 | Shelton et al. |
| 2007/0203477 A1 | 8/2007 | Lechot |
| 2007/0205681 A1 | 9/2007 | Corbin |
| 2007/0277988 A1 | 12/2007 | Stoetzer |
| 2007/0290458 A1 | 12/2007 | Chuang |
| 2008/0003537 A1 | 1/2008 | Papanek et al. |
| 2008/0004617 A1 | 1/2008 | Hagg et al. |
| 2008/0045972 A1 | 2/2008 | Wagner et al. |
| 2008/0054575 A1 | 3/2008 | Hartmann |
| 2008/0058801 A1 | 3/2008 | Taylor et al. |
| 2008/0064007 A1 | 3/2008 | Carron et al. |
| 2008/0070704 A1 | 3/2008 | Muller et al. |
| 2008/0082138 A1 | 4/2008 | Smits |
| 2008/0097409 A1 | 4/2008 | Stephens |
| 2008/0110958 A1 | 5/2008 | McKenna et al. |
| 2008/0118315 A1 | 5/2008 | Brunson |
| 2008/0145162 A1 | 6/2008 | Mihic |
| 2008/0146353 A1 | 6/2008 | Boffelli et al. |
| 2008/0167736 A1 | 7/2008 | Swayze et al. |
| 2008/0171603 A1 | 7/2008 | Kneeshaw et al. |
| 2008/0179841 A1 | 7/2008 | Chen |
| 2008/0188841 A1 | 8/2008 | Tomasello et al. |
| 2008/0197167 A1 | 8/2008 | Viola et al. |
| 2008/0199356 A1 | 8/2008 | Suter |
| 2008/0208195 A1 | 8/2008 | Shores et al. |
| 2008/0220392 A1 | 9/2008 | Carron et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0257935 A1 | 10/2008 | Viola |
| 2008/0292418 A1 | 11/2008 | Kay et al. |
| 2008/0308603 A1 | 12/2008 | Shelton et al. |
| 2008/0314642 A1 | 12/2008 | Rodney |
| 2009/0022562 A1 | 1/2009 | Chin |
| 2009/0030271 A1 | 1/2009 | Foley et al. |
| 2009/0042162 A1 | 2/2009 | Pond |
| 2009/0054890 A1 | 2/2009 | DeCarlo |
| 2009/0082772 A1 | 3/2009 | Ferreira |
| 2009/0090763 A1 | 4/2009 | Zemlok et al. |
| 2009/0118784 A1 | 5/2009 | Alexander et al. |
| 2009/0138006 A1 | 5/2009 | Bales et al. |
| 2009/0143785 A1 | 6/2009 | Chang et al. |
| 2009/0145947 A1 | 6/2009 | Scirica et al. |
| 2009/0171147 A1 | 7/2009 | Lee et al. |
| 2009/0179063 A1 | 7/2009 | Milliman et al. |
| 2009/0194954 A1 | 8/2009 | Hsu |
| 2009/0221873 A1 | 9/2009 | McGrath |
| 2009/0224492 A1 | 9/2009 | Lin |
| 2009/0228087 A1 | 9/2009 | Malinowski |
| 2009/0234490 A1 | 9/2009 | Suprock et al. |
| 2009/0248126 A1 | 10/2009 | Nippoldt et al. |
| 2009/0254094 A1 | 10/2009 | Knapp et al. |
| 2009/0261539 A1 | 10/2009 | Paulsen |
| 2009/0273146 A1 | 11/2009 | Dezheng et al. |
| 2009/0279973 A1 | 11/2009 | Erickson |
| 2009/0311061 A1 | 12/2009 | Santamarina et al. |
| 2009/0315281 A1 | 12/2009 | Tuauden et al. |
| 2010/0015568 A1 | 1/2010 | Carron et al. |
| 2010/0052269 A1 | 3/2010 | Zaiser et al. |
| 2010/0056986 A1 | 3/2010 | Allen et al. |
| 2010/0069942 A1 | 3/2010 | Shelton, IV |
| 2010/0081108 A1 | 4/2010 | Webster |
| 2010/0089974 A1 | 4/2010 | Shelton, IV |
| 2010/0094260 A1 | 4/2010 | Cude et al. |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |

(56) References Cited

U.S. PATENT DOCUMENTS

| | | |
|---|---|---|
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 101856251 A | 10/2010 |
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1723913 A1 | 11/2006 |
| EP | 1759652 A2 | 3/2007 |
| EP | 1772105 A1 | 4/2007 |
| EP | 1 813 199 A1 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1952769 A2 | 8/2008 |
| EP | 2005898 A2 | 12/2008 |
| EP | 2044890 A1 | 4/2009 |
| EP | 2090247 A1 | 8/2009 |
| EP | 2098170 A2 | 9/2009 |
| EP | 2100562 A2 | 9/2009 |
| EP | 2165664 A2 | 3/2010 |
| EP | 2 236 098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2 462 880 A2 | 6/2012 |
| EP | 2462878 A1 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2815705 A1 | 12/2014 |
| ES | 2333509 A1 | 2/2010 |
| FR | 2861574 A1 | 5/2005 |
| JP | 08-038488 | 2/1996 |
| JP | 2003310629 A | 11/2003 |
| JP | 2005-125075 A | 5/2005 |
| JP | 2009106752 A | 5/2009 |
| KR | 20120022521 A | 3/2012 |
| WO | 99/15086 A1 | 4/1999 |
| WO | 03/000138 A2 | 1/2003 |
| WO | 03/030743 A2 | 4/2003 |
| WO | 2003065916 A1 | 8/2003 |
| WO | 2003/090630 A2 | 11/2003 |
| WO | 2007/014355 A2 | 2/2007 |
| WO | 2007016290 A2 | 2/2007 |
| WO | 2007/137304 A2 | 11/2007 |
| WO | 2009/039506 A1 | 3/2009 |
| WO | 2009/143092 A1 | 11/2009 |
| WO | 2009/149234 A1 | 12/2009 |
| WO | 2011/108840 A2 | 9/2011 |
| WO | 2012/040984 A1 | 4/2012 |

OTHER PUBLICATIONS

Extended European Search Report from EP Application No. 13189026.1 dated Jan. 31, 2014.
Extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
Extended European Search Report corresponding to EP 10252037.6, dated Mar. 9, 2011; (3 pp.).
European Search Report corresponding to EP 11250771, dated Feb. 17, 2012; (3 pp.).
Extended European Search Report corresponding to EP No. 11 17 8021.9, dated Jun. 4, 2013; (3 pp).
Extended European Search Report corresponding to EP No. 13 16 30317, completed Jun. 27, 2013 and dated Jul. 15, 2013; (8 pp).
Extended European Search Report corresponding to EP No. 12 18 61771, completed Aug. 14, 2013 and dated Aug. 23, 2013; (8 pp).
Partial European Search Report corresponding to EP No. 13 17 1742.3, completed Sep. 17, 2013 and dated Sep. 25, 2013; (8 pp).

(56) References Cited

OTHER PUBLICATIONS

Partial European Search Report corresponding to EP No. 13 17 2400.7, completed Sep. 18, 2013 and dated Oct. 1, 2013; (7 pp).
Extended European Search Report corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).
Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
Extended European Search Report corresponding to EP No. 08 25 2703.7, completed Oct. 23, 2008 and dated Oct. 31, 2008; (7 pp).
Japanese Laid Open Publication No. 2009-112783 dated May 28, 2009.
Japanese National Phase PCT Laid open Publication No. 2009-502352 dated Jan. 29, 2009.
Chinese Office Action for Application No. 201510330707.3 dated Sep. 28, 2016.
European Office Action for EP 11250771.0 dated Oct. 18, 2016.
Chinese Office Action dated Apr. 28, 2017 issued in corresponding Chinese Application No. 201510330707.3.
Canadian Office Action dated May 4, 2017 issued in corresponding Canadian Application No. 2,750,572.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action, and English language translation, issued in Application No. CN 201510330707.3 dated Nov. 6, 2017 (11 pages).
Japanese Office Action dated Mar. 29, 2018 issued in corresponding JP Appln. No. 2017-091837.

ADAPTER FOR POWERED SURGICAL DEVICES

CROSS-REFERENCE TO RELATED APPLICATIONS

This application is a Continuation of U.S. patent application Ser. No. 13/621,859 filed Sep. 18, 2012, now U.S. Pat. No. 9,282,963, which is a Continuation of U.S. patent application Ser. No. 13/216,330 filed Aug. 24, 2011, now U.S. Pat. No. 8,292,150, which claims benefit of and priority to U.S. Provisional Application No. 61/409,132 filed Nov. 2, 2010, and the disclosures of each of the above-identified applications are hereby incorporated by reference in their entirety.

BACKGROUND

1. Technical Field

The present disclosure relates to a surgical device and, more particularly, to an adapter assembly for selectively interconnecting a surgical end effector and a powered actuator device.

2. Background of Related Art

A number of proprietary drive systems for operating surgical devices that clamp tissue between opposing jaw structures and then join tissue by surgical fasteners have been developed by various surgical device manufacturers. Many of the existing surgical end effectors used in performing, for example, endo-gastrointestinal anastomosis procedures, end-to-end anastomosis procedures and transverse anastomosis procedures, typically require linear driving force in order to be operated.

Generally, the stapling operation is effected by cam bars that travel longitudinally through the staple cartridge and act upon staple pushers to sequentially eject the staples from the staple cartridge. Such cam bars are typically actuated by a trigger squeezed by an operator or a powered actuator device that provides rotary motion to deliver driving force. In the case of a powered actuator device that uses rotary motion to deliver driving force the rotary motion is not compatible with surgical end effectors that require linear driving force.

As such, in order to make the linear driven surgical end effectors compatible with the powered actuator devices that use rotary motion to deliver driving force, adapter assemblies that convert the output features of the powered actuator devices to match the work input requirements of end effectors are required.

SUMMARY

In accordance with an embodiment of the present disclosure, there is provided an adapter assembly for selectively interconnecting a surgical end effector and a powered actuator device. The adapter assembly includes a first drive converter assembly configured to convert a rotation of a first drive shaft of the powered actuator device into an axial translation of a first drive member of the surgical end effector and a second drive converter assembly configured to convert a rotation of a second drive shaft of the powered actuator device into an axial translation of a second drive member of the surgical end effector. The first drive converter assembly is at least partially disposed within the second drive converter assembly, wherein the first drive converter assembly and the second drive converter assembly are configured to rotate and translate independent of each other.

The adapter assembly may further include first and second drive rods configured to be coupled with the rotatable first and second drive shafts of the powered actuator device, respectively. The first drive rod engages the first drive converter assembly and the second drive rod engages the second drive converter assembly.

The first and second drive rods may each include a pinion gear portion. The first drive converter assembly may include an actuation shaft defining a worm gear portion. The first drive rod supports a pinion gear portion, wherein the worm gear portion of the actuation shaft engages the pinion gear portion of the first drive rod, whereby rotation of the first drive shaft of the powered actuator device rotates the pinion gear portion of the first drive rod to effectuate axial translation of the actuation shaft which in turn axially translates the first drive member of the surgical end effector.

Similarly, the second drive converter assembly may include an elongate tube defining a worm gear portion. The second drive rod supports a pinion gear portion, wherein the worm gear portion of the elongate tube engages the pinion gear portion of the second drive rod, whereby rotation of the second drive shaft of the powered actuator device rotates the pinion gear portion of the second drive rod to effectuate axial translation of the elongate tube which in turn axially translates the second drive member of the surgical end effector.

The first and second drive rods may be flexible and capable of transmitting rotational forces. In addition, a distal end of the adapter assembly may be configured for a selective, detachable fitting with the surgical end effector.

In accordance with another aspect of the present disclosure, there is provided a surgical device including a powered actuator device including at least two rotatable drive shafts, a surgical end effector including at least two axially translatable drive members and an adapter assembly including a first drive converter assembly and a second drive converter assembly. The first drive converter assembly is configured to convert rotation of a first drive shaft of the powered actuator device into an axial translation of a first drive member of the surgical end effector. The second drive converter assembly is configured to convert rotation of a second drive shaft of the powered actuator device into an axial translation of a second drive member of the surgical end effector, wherein the first drive converter assembly is at least partially disposed within the second drive converter assembly.

The adapter assembly may further include first and second drive rods configured to be operatively coupled with the rotatable first and second drive shafts of the powered actuator device, respectively. The first drive rod engages the first drive converter assembly and the second drive rod engages second drive converter assembly.

The first and second drive rods may each include a pinion gear portion. Moreover, the first drive converter assembly may include an actuation shaft defining a worm gear portion, wherein the first drive rod supports a pinion gear portion. The worm gear portion of the actuation shaft engages the pinion gear portion of the first drive rod, whereby rotation of the first drive shaft of the powered actuator device rotates the pinion gear portion of the first drive rod to effectuate axial translation of the actuation shaft which in turn axially translates the first drive member of the surgical end effector.

Similarly, the second drive converter assembly may include an elongate tube defining a worm gear portion, wherein the second drive rod supports a pinion gear portion. The worm gear portion of the elongate tube engages the pinion gear portion of the second drive rod, whereby rotation of the second drive shaft of the powered actuator device rotates the pinion gear portion of the second drive rod to effectuate axial translation of the elongate tube which in turn axially translates the second drive member of the surgical end effector.

The first and second drive rods may be flexible and capable of transmitting rotational forces. In addition, a distal end of the adapter assembly may be configured for a selective, detachable fitting with the surgical end effector.

BRIEF DESCRIPTION OF THE DRAWINGS

The foregoing objects, features and advantages of the disclosure will become more apparent from a reading of the following description in connection with the accompanying drawings, in which.

DETAILED DESCRIPTION OF EMBODIMENTS

Embodiments of the presently disclosed adapter assemblies for surgical devices are described in detail with reference to the drawings, in which like reference numerals designate identical or corresponding elements in each of the several views. In the drawings and in the description that follows, the term "proximal," as is traditional, will refer to the end of the stapling apparatus which is closest to the operator, while the term "distal" will refer to the end of the apparatus which is farthest from the operator.

Figure 1:
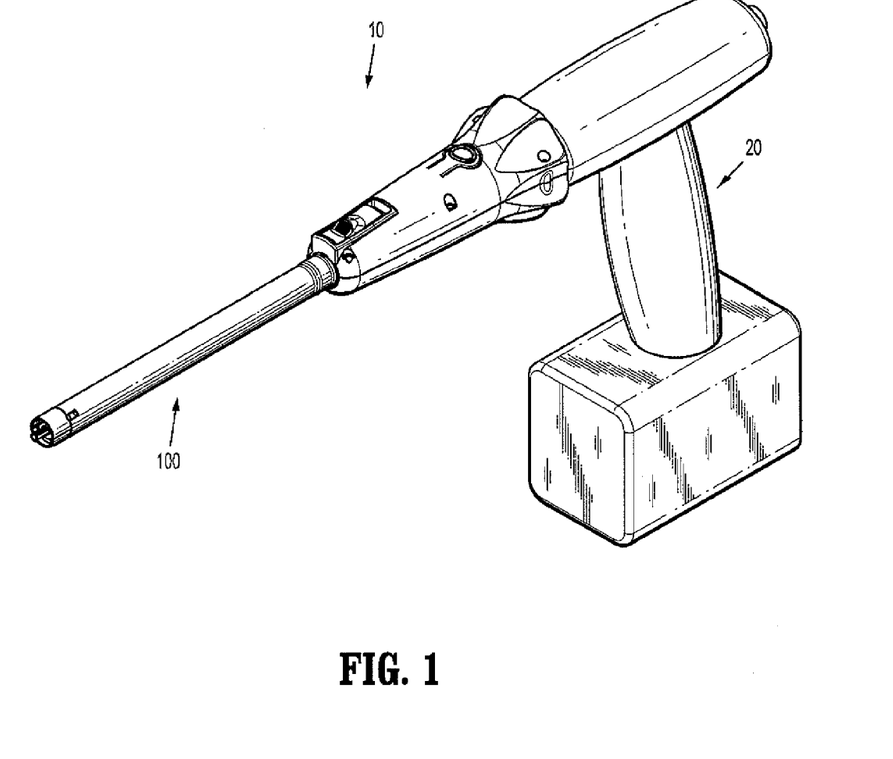
FIG. 1 is a perspective view of a surgical device including an adapter assembly according to an embodiment of the present disclosure.

Referring now to FIG. 1, there is disclosed a powered surgical instrument generally referred to as 10. In the interest of brevity, this disclosure will focus primarily on a mechanical adapter assembly 100 for selectively interconnecting a surgical end effector and a powered actuator device 20. For a detailed description of the construction and operation of exemplary powered surgical instrument 10 for use with adapter assembly 100, reference may be made to U.S. Patent Application Publication No. 2007/0023477, the entire content of which is incorporated herein by reference.

Figure 2:
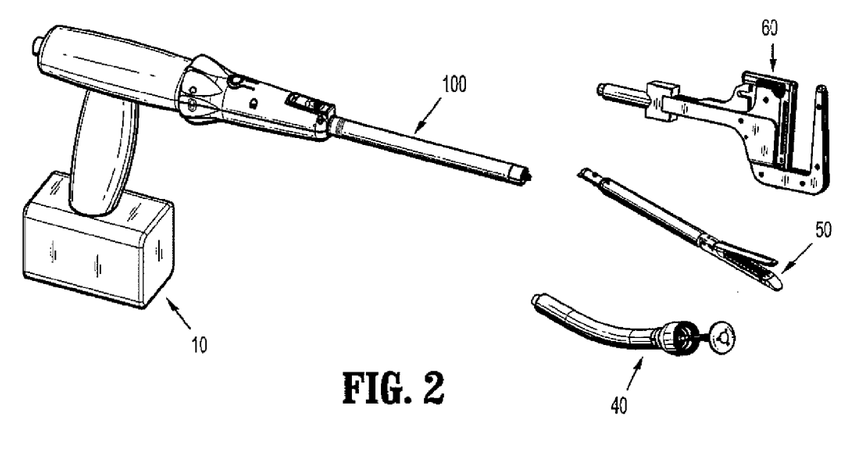
FIG. 2 is a perspective view of the surgical device of FIG. 1, illustrating the potential use with various surgical end effectors.
Figure 3:
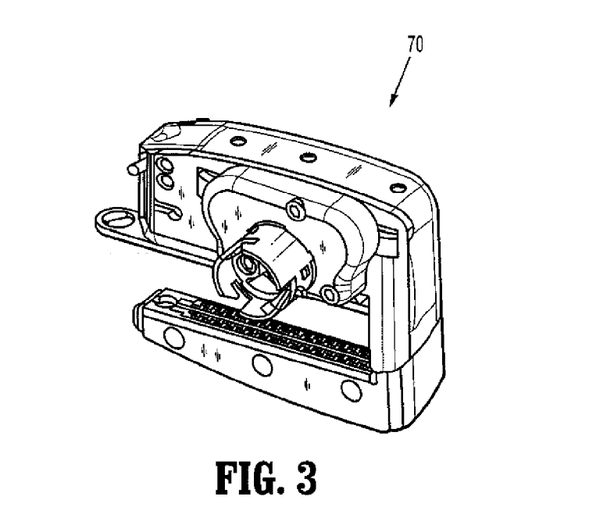
FIG. 3 is a perspective view of a right angled linear cutter/stapler end effector for use with an adapter assembly according to an embodiment of the present disclosure.

With reference to FIGS. 1-3, powered surgical instrument 10 generally includes a powered actuator device 20 and mechanical adapter assembly 100 selectively interconnecting any one of surgical end effectors 40, 50, 60, 70 and powered actuator device 20. Any one of end effectors 40, 50, 60, 70 may be releasably secured to a distal end of adapter assembly 100. Each end effector 40, 50, 60, 70 includes a cartridge assembly housing a plurality of surgical fasteners or staples and an anvil assembly movably secured in relation to the cartridge assembly. Powered actuator device 20 includes a housing, at least one drive motor, at least one energy source for powering the at least one drive motor, and at least one rotatable drive shaft connected to the at least one drive motor. In use, the actuation of the drive motor results in an actuation of an end effector 40, 50, 60, 70 attached thereto, to apply staples to tissue and to optionally cut tissue.

Figure 4:
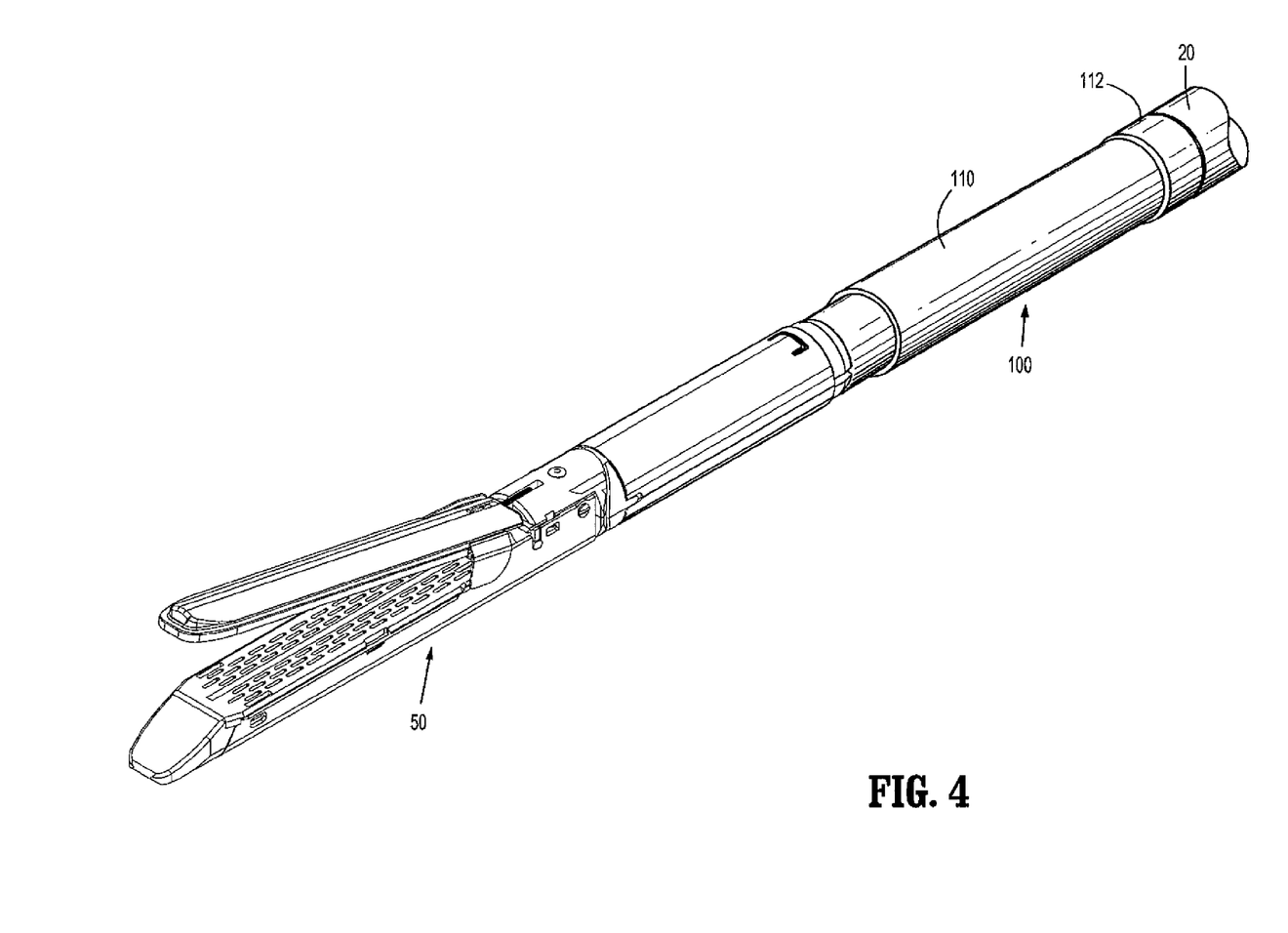
FIG. 4 is a perspective view of an adapter assembly according to an embodiment of the present disclosure having a surgical end effector connected thereto.
Figure 5:
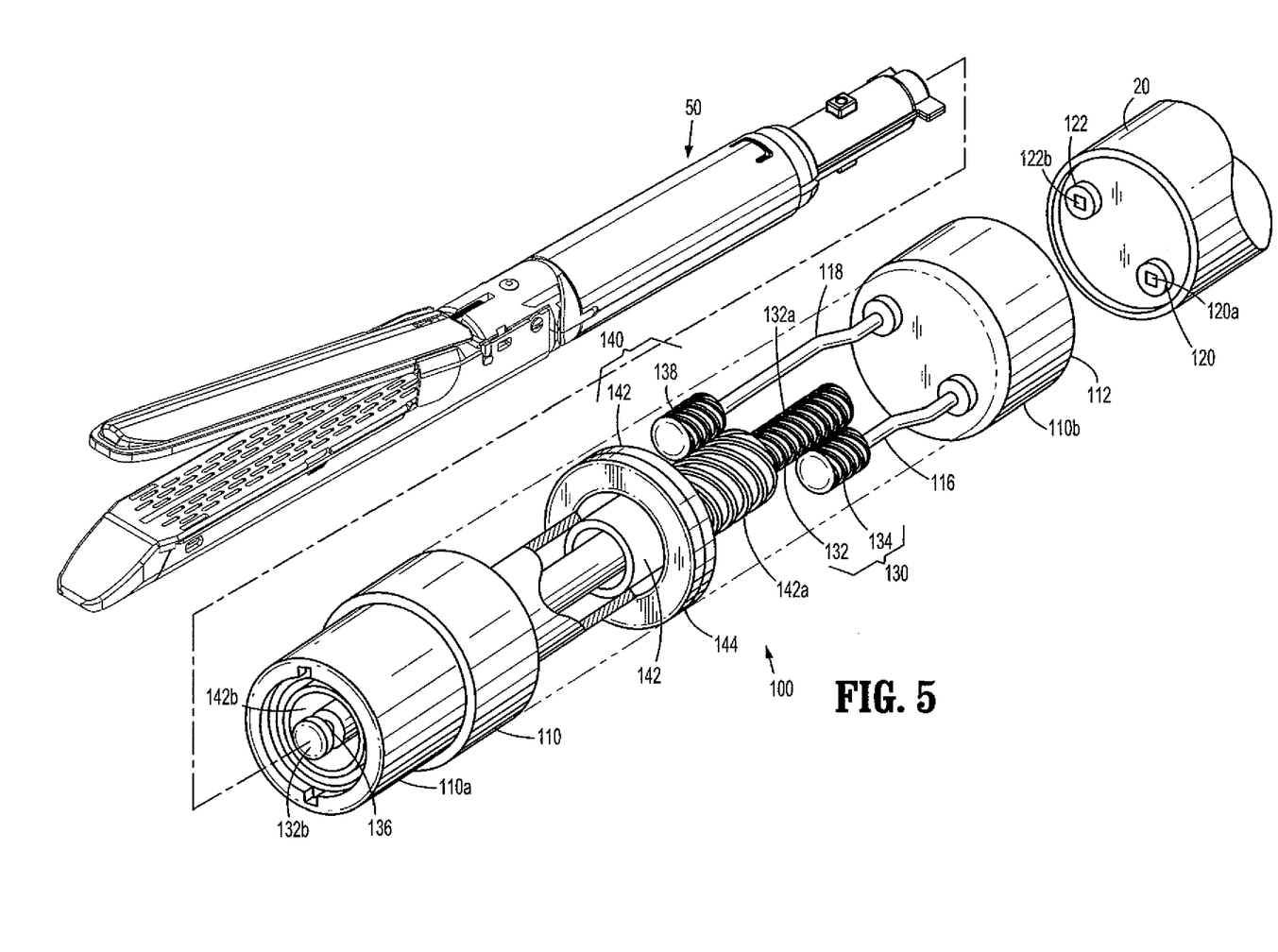
FIG. 5 is an enlarged perspective view of the adapter assembly of FIG. 4 shown with an outer tube removed therefrom.
Figure 6:
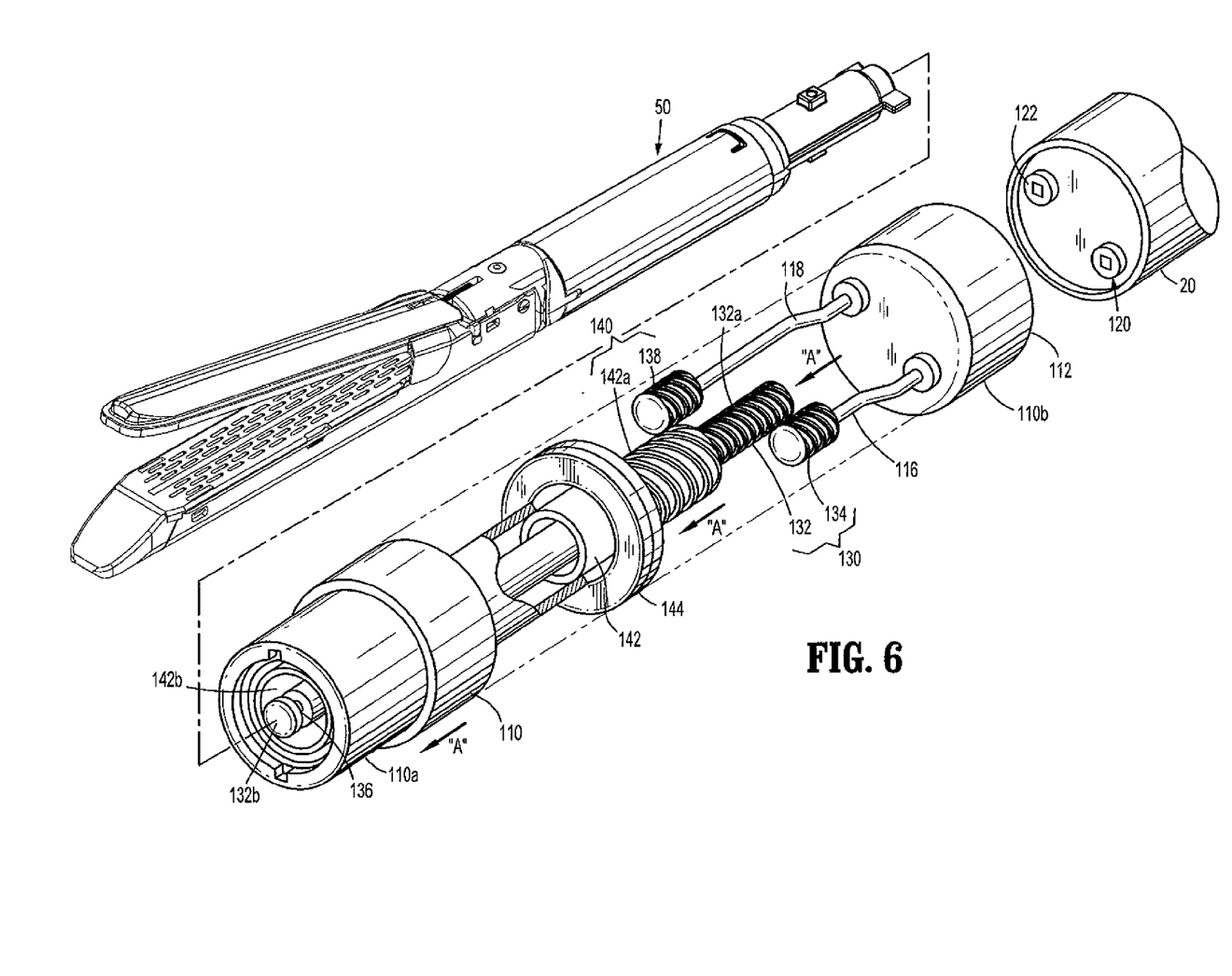
FIG. 6 is an enlarged perspective view of the adapter assembly of FIG. 5 illustrating an independent axial translation of an actuation shaft and an inner tube thereof.

With reference to FIGS. 4, 5 and 6, an adapter assembly in accordance with an embodiment of the present disclosure is shown generally as 100. As shown in FIGS. 4-6, adapter assembly 100 is operatively connected to a distal end of powered actuator device 20, and surgical end effector 50 is selectively coupled to a distal end of adapter assembly 100. However, adapter assembly 100 is configured to operatively interconnect any one of a number of surgical end effectors to powered actuator device 20, as seen in FIG. 2. For example, adapter assembly 100 may operatively interconnect and couple powered actuator device 20 to an endo-gastrointestinal anastomosis end effector 40 or a transverse anastomosis end effector 60, both of which require linear driving force.

Each of end effectors 40, 50, 60 includes an axially translatable drive member to fire end effectors 40, 50, 60 to expel staples contained in the cartridge assembly for formation against the anvil assembly and/or to actuate a knife blade along the staple line. End effectors 40, 50, 60 may include an additional axially translatable drive member that is configured to open and close the jaw assemblies by approximating at least one of the anvil assembly and the cartridge assembly to and away from one another. The additional axially translatable drive member may also be configured to cause articulation of end effectors 40, 50, 60.

Adapter assembly 100 may be configured to operatively interconnect with a surgical end effector requiring a linear driving force, but may also be adaptable to be operatively coupled to an end effector requiring a rotational driving force for an operation thereof, such as, for example, a right angled linear cutter/stapler end effector 70, as shown in FIG. 3. Right angled linear cutter/stapler end effector 70 includes a rotatable drive member for firing end effector 70 to expel staples contained in the cartridge assembly for formation against the anvil assembly. End effector 70 may include additional rotatable drive members to actuate a knife blade along the staple line and/or to open and close the jaw assemblies by approximating at least one of the anvil assembly and the cartridge assembly to and away from one another.

With reference still to FIGS. 4-6, a detailed description of the construction and operation of adapter assembly 100 is provided. Adapter assembly 100 includes a tube housing 110 configured to house the components of adapter assembly 100 and dimensioned such that tube housing 110 may pass through a typical trocar port, cannula or the like. Tube housing 110 includes a distal end portion 110a that is operatively coupled to end effector 50 and a proximal end portion 110b that is coupled to powered actuator device 20.

In particular, as seen in FIGS. 5 and 6, adapter assembly 100 further includes a drive coupling assembly 112 at a proximal end portion thereof, which operatively couples adapter assembly 100 to powered actuator device 20. Drive coupling assembly 112 includes rotatably supported and distally extending first and second proximal drive shafts 116, 118, respectively. Proximal drive shafts 116, 118 may be made flexible to act as shock absorbers allowing for reduced peak loads, yet sufficiently rigid to transmit rotational forces. First and second proximal drive shafts 116, 118 each include at a proximal portion thereof a tapered neck portion (not shown) having a non-circular cross-sectional profile, e.g., square shaped. Each of first and second proximal drive shafts 116, 118 is provided with a biasing means (not shown) disposed about the respective neck portion and a sleeve (not shown) disposed proximal of the biasing means. The sleeves each define a bore having a cross-sectional profile that corresponds to that of the neck portion of proximal drive shafts 116, 118. The distal ends of the first and second drive shafts of powered actuator device 20 include coupling cuffs 120, 122, each defining a recess 120a, 122a corresponding to the non-circular cross-sectional profile of the neck portion of proximal drive shafts 116, 118. Coupling cuffs 120, 122 of actuator device 20 engage the proximal end portions (not shown) of proximal drive shafts 116, 118 (wherein each proximal end portion of the proximal drive shafts 116, 118 has a non-circular cross-sectional profile for engaging respective recess 120a, 122a of coupling cuffs 120, 122), whereby rotation of drive shafts (not shown) of powered actuator device 20 results in concomitant rotation of coupling cuffs 120, 122 and concomitant rotation of first and second proximal drive shafts 116, 118.

With continued reference to FIGS. 5 and 6, adapter assembly 100 further includes first and second drive converter assemblies 130, 140. Each drive converter assembly 130, 140 is configured to convert rotation of respective first and second drive shafts of powered actuator device 20 and concomitant rotation of respective first and second proximal drive shafts 116, 118 into axial translation of respective drive members of end effector 50.

The first drive converter assembly 130 includes an actuation shaft 132 translatably supported for axial reciprocation within an inner tube 142 of drive converter assembly 140 by any number of appropriately positioned and sized bearings and/or bushings (not shown). The coaxial relationship of actuation shaft 132 and inner tube 142 allows for axially rotational displacement thereof without adverse end effector 50 actuation or spatial conflict therebetween. Actuation shaft 132 includes a worm-gear portion 132a at a proximal end region of actuation shaft 132 and a distal end portion 132b defining a connection member 136 configured for selective engagement with an axially translatable drive member of end effector 50. First drive converter assembly 130 further includes a pinion or worm gear portion 134 provided at a distal end portion of first proximal drive shaft 116. Pinion gear portion 134 engages worm gear portion 132a at a proximal end region of actuation shaft 132.

In operation, as seen in FIGS. 5 and 6, the activation/rotation of a first drive shaft (not shown) of powered surgical device 20 results in concomitant rotation of first proximal drive shaft 116 of adapter assembly 100. As first proximal drive shaft 116 is rotated, first proximal drive shaft 116 causes rotation of pinion gear portion 134. Since pinion gear portion 134, at a distal end portion of first proximal drive shaft 116, engages worm gear portion 132a of actuation shaft 132, rotation of pinion gear portion 134 causes axial translation of actuation shaft 132. It is contemplated that the actuation shaft 132 is supported by any number of appropriately positioned and sized bearings and bushings (not shown) that enable axial translation in the direction of "A" as shown in FIG. 6. Accordingly, with connection member 136 of actuation shaft 132 connected to a first drive member of end effector 50, axial translation of actuation shaft 132 causes concomitant axial translation of the first drive member of end effector 50 to effectuate an operation and/or function thereof, such as, for example, firing of the end effector 50.

Upon completion of the operation and/or function of the first drive member of end effector 50, e.g., firing of end effector 50, actuation shaft 132 may be retracted to its initial position for subsequent operation thereof. The first drive shaft (not shown) of powered surgical device 20 is reactivated causing rotation thereof in the direction opposite to that when actuation shaft 132 was axially translated in the distal direction. The concomitant rotation of first proximal drive shaft 116 of adapter assembly 100 causes rotation of pinion gear portion 134. Pinion gear portion 134 engages worm gear portion 132a of actuation shaft 132 and causes axial translation of actuation shaft 132 in a proximal direction until actuation shaft 132 reaches the initial position.

With continued reference to FIGS. 5 and 6, second drive converter assembly 140 includes an inner tube 142 rotatably supported by rotary plates 144 or by any number of appropriately positioned and sized bearings or bushings (not shown) for axial reciprocation of inner tube 142 within tube housing 110. Inner tube 142 includes a worm-gear portion 142a at a proximal end region of inner tube 142 and a distal end portion 142b disposed at a distal end of tube housing 110. Second drive converter assembly 140 further includes a pinion or worm gear 138 provided at a distal end portion of second proximal drive shaft 118. Worm-gear portion 142a of inner tube 142 engages pinion gear 138 for axial reciprocation of inner tube 142 within tube housing 110.

In operation, as seen in FIGS. 5 and 6, the activation/rotation of a second drive shaft (not shown) of powered surgical device 20 results in concomitant rotation of second proximal drive shaft 118 of adapter assembly 100. As second proximal drive shaft 118 is rotated due to rotation of the second drive shaft of powered actuator device 20, pinion gear 138 of second drive converter assembly 150 is caused to be rotated. Since pinion gear 138, at a distal end portion of second proximal drive shaft 118, engages worm gear portion 142a of inner tube 142, rotation of pinion gear portion 138 causes axial translation of inner tube 142 independently of actuation shaft 132, in the direction of arrow "A" as shown in FIG. 6. Accordingly, as inner tube 142 is translated axially, with the distal end of inner tube 142 connected to a second drive member of end effector 50, inner tube 142 causes concomitant axial translation of the second drive member of end effector 50 to effectuate an additional operation thereof, such as, for example, articulation of the end effector and/or approximation of the pair of jaws, independent of the operation effected by actuation shaft 132.

Upon completion of the operation and/or function of the second drive member of end effector 50, e.g., articulation of end effector 50 and/or approximation of the pair of jaws, inner tube 142 may be retracted to its initial position for subsequent operation thereof. The second drive shaft (not shown) of powered surgical device 20 is reactivated causing rotation thereof in the direction opposite to that when inner tube 142 was axially translated in the distal direction. The concomitant rotation of second proximal drive shaft 118 of adapter assembly 100 causes rotation of pinion gear portion 138. Pinion gear portion 138 engages worm gear portion 142a of inner tube 142 and causes axial translation of inner tube 142 in a proximal direction until inner tube 142 reaches the initial position.

Actuation shaft 132 is dimensioned to be concentrically arranged within inner tube 142 which allows for a compact design of adapter assembly 100 and independent coaxial translation of actuation shaft 132 with respect to inner tube 142. Actuation shaft 132 may further include a pair of flanges (not shown) extending radially, so that the pair of flanges restrict the range of axial translation of actuation shaft 132 in conjunction with an inwardly extending flange (not shown) formed within inner tube 142, whereby a proximal end of actuation shaft 132 is prevented from being driven into drive coupling assembly 112 and/or from distally disengaging pinion gear 134 of first proximal drive shaft 116. Moreover, the placement of the flanges may be tailored to meet the needs of a particular end effector to take into account, e.g., the required travel distance of the particular axially translatable drive member of the surgical end effector.

Similarly, inner tube 142 may further include radially extending flanges (not shown) such that inner tube 142 reciprocates axially inside tube housing 110 within a predetermined ranged. Under such design, inner tube 142 is prevented from being driven distally into pinion gear 134 on first proximal drive shaft 116 and from distally disengaging pinion gear 138 on second proximal drive shaft 122. Moreover, such design allows inner tube 142 to translate only the distance required to effectuate an operation of the drive member of end effector 50.

In accordance with the present disclosure, it is contemplated that the adapter assembly 100 may incorporate a transmission or gearing portion to optimize the rotational speed and torque or the linear speed and force to control and manipulate specific end effectors. Furthermore, the pitch and helix angle of the worm gear can be configured to provide additional speed and/or force refinements as needed.

It is further contemplated that the proximal and distal ends of adapter assembly 100 may be operatively coupled to powered actuator device 20 and any one of end effectors 40, 50, 60, 70, respectively, using a variety of attachment features, such as, for example, a bayonet coupling, latch, detent or snap-fit. In addition, adapter assembly 100 may include a lock mechanism (not shown) configured to fix the axial position and radial orientation of actuation shaft 132 for the connection and disconnection of end effectors 40, 50, 60, 70 thereto. Still further, axial rotation of the entire tube housing 110 can be accomplished by engaging rotary power from the power actuator (if available) or by manually turning the tube housing.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

What is claimed is:

1. An adapter assembly for selectively interconnecting a surgical end effector and a powered actuator device, the adapter assembly comprising:
    an actuation shaft configured to convert a rotation of a first drive shaft of a powered actuator device into an axial movement of a first drive member of a surgical end effector; and
    an elongate tube configured to convert a rotation of a second drive shaft of a powered actuator device into an axial movement of a second drive member of a surgical end effector, wherein the actuation shaft is at least partially disposed within the elongate tube and the actuation shaft and the elongate tube are rotatably and axially movable relative to each other.

2. The adapter assembly of claim 1, further comprising:
    a first drive rod configured to engage the first drive shaft of a powered actuator device and the actuation shaft; and
    a second drive rod configured to engage the second drive shaft of a powered actuator device and the elongate tube.

3. The adapter assembly of claim 2, wherein each of the first and second drive rods includes a pinion gear portion.

4. The adapter assembly of claim 3, wherein the actuation shaft includes a worm gear portion configured to engage the pinion gear portion of the first drive rod.

5. The adapter assembly of claim 3, wherein the elongate tube includes a worm gear portion configured to engage the pinion gear portion of the second drive rod.

6. The adapter assembly of claim 2, wherein the first and second drive rods are flexible and are configured to transmit rotational forces.

7. The adapter assembly of claim 1, wherein a distal end of the adapter assembly is configured for a selective, detachable coupling with the surgical end effector and a proximal end of the adapter assembly is configured for a selective, detachable coupling with the powered actuator device.

8. A surgical instrument comprising:
    a surgical end effector including a first drive member and a second drive member;
    a powered actuator device including a first drive shaft and a second drive shaft; and
    an adapter assembly configured to interconnect the surgical end effector and the powered actuator device, the adapter assembly including:
        an actuation shaft configured to convert a rotation of the first drive shaft into an axial movement of the first drive member; and
        an elongate tube configured to convert a rotation of the second drive shaft into an axial movement of the second drive member, wherein the actuation shaft is at least partially disposed within the elongate tube and the actuation shaft and the elongate tube are rotatably and axially movable relative to each other.

9. The surgical instrument of claim 8, wherein the adapter assembly further includes:
    a first drive rod configured to engage the first drive shaft and the actuation shaft; and
    a second drive rod configured to engage the second drive shaft and the elongate tube.

10. The surgical instrument of claim 9, wherein each of the first and second drive rods includes a pinion gear portion.

11. The surgical instrument of claim 10, wherein the actuation shaft includes a worm gear portion configured to engage the pinion gear portion of the first drive rod, such that rotation of the first drive shaft of the powered actuator device rotates the pinion gear portion of the first drive rod to effectuate axial movement of the actuation shaft, which in turn, axially moves the first drive member of the surgical end effector.

12. The surgical instrument of claim 10, wherein the elongate tube includes a worm gear portion configured to engage the pinion gear portion of the second drive rod, such that rotation of the second drive shaft of the powered actuator device rotates the pinion gear portion of the second drive rod to effectuate axial movement of the elongate tube, which in turn, axially moves the second drive member of the surgical end effector.

13. The surgical instrument of claim 9, wherein the first and second drive rods are flexible and are configured to transmit rotational forces.

14. The surgical instrument of claim 8, wherein a distal end of the adapter assembly is configured for a selective, detachable fitting with the surgical end effector and a proximal end of the adapter assembly is configured for a selective, detachable fitting with the powered actuator device.

15. The surgical instrument of claim 8, wherein the surgical end effector includes an anvil assembly and a cartridge assembly having at least one tissue fastener.

16. The surgical instrument of claim 15, wherein the first drive member is configured to eject the at least one tissue fastener from the cartridge assembly in response to the axial movement of the first drive member.

17. The surgical instrument of claim 15, wherein the second drive member is configured to move the anvil assembly and the cartridge assembly relative to each other in response to the axial movement of the second drive member.

\* \* \* \* \*